United States Patent [19]

Scher et al.

[11] 4,155,741

[45] May 22, 1979

[54] STABLE SUSPENSION SYSTEM FOR MICROENCAPSULATED FLOWABLE FORMULATIONS, AND METHOD OF PREPARING STABLE SUSPENSION OF MICROCAPSULES

[75] Inventors: Herbert B. Scher, Moraga; Robert J. Cochran, Fairfield, both of Calif.

[73] Assignee: Stauffer Chemical Company, Westport, Conn.

[21] Appl. No.: 465,784

[22] Filed: May 1, 1974

[51] Int. Cl.$^2$ .......................... A01H 3/04; A01N 5/00; A01N 17/00; A01N 23/00
[52] U.S. Cl. ........................................ 71/65; 71/64 C; 71/80; 71/100; 71/118; 71/DIG. 1; 252/310; 252/315; 252/316; 424/32; 424/222; 424/357
[58] Field of Search ....................... 252/310, 315, 316; 71/64 C, 65, 80, DIG. 1; 424/357; 423/629

[56] References Cited

U.S. PATENT DOCUMENTS

| 1,112,755 | 10/1914 | Bergstrom | 424/10 |
|---|---|---|---|
| 1,540,446 | 6/1925 | Wilson | 423/629 X |
| 3,068,185 | 12/1962 | Stamberger | 117/100 S X |
| 3,509,066 | 4/1970 | Jacobs et al. | 252/313 R |
| 3,575,882 | 4/1971 | Vandegaer et al. | 252/316 |
| 3,576,760 | 4/1971 | Gould et al. | 424/32 |
| 3,577,515 | 5/1971 | Vandegaer | 252/316 X |

Primary Examiner—Richard D. Lovering
Attorney, Agent, or Firm—Harry A. Pacini

[57] ABSTRACT

Stable suspension-buffer system for aqueous suspensions of microencapsulated materials which can be obtained by using aluminum hydroxide or ferric hydroxide as the suspending and buffering agent, together with a sequestering agent, a second suspending agent, thereby preventing separation and caking in microcapsule flowable formulations.

16 Claims, No Drawings

STABLE SUSPENSION SYSTEM FOR MICROENCAPSULATED FLOWABLE FORMULATIONS, AND METHOD OF PREPARING STABLE SUSPENSION OF MICROCAPSULES

FIELD OF THE INVENTION

This invention relates to the preparation of stable aqueous suspensions of polyurea-encapsulated materials such as insecticides, pesticides, fungicides, fumigants and the like, by the use of aluminum hydroxide or ferric hydroxide as the suspending agent and buffering agent, together with sequestering agents and other suspending agents.

BACKGROUND OF THE INVENTION

In recent developments, many materials have been encapsulated with polymers, especially polyureas. This development is extremely significant from the standpoint of safety and handling of otherwise toxic materials. Often the encapsulated materials have provided superior results in the applications for which they are intended. A convenient method of application of the encapsulated materials is by spraying water dispersions. It has been found that the suspensions of encapsulated materials are not stable and tend to separate rapidly, even when conventional dispersants are used, thereby resulting in caking of the microencapsulated material.

The application of suspensions which have separated is extremely difficult under field conditions and, therefore, stable suspensions are desirable. Polyurea and other encapsulated materials on separating and standing, cake excessively, such that the particles cannot be redispersed with equipment normally used in field applications. This produces an unsatisfactory condition for actual field use.

Reference is made to Belgian Pat. No. 796,746 assigned to Stauffer Chemical Company, published Sept. 14, 1973. The aforementioned patent describes a method for encapsulating various water-immiscible materials employing an organic isocyanate intermediate to form a polyurea capsule enclosure around a water-immiscible material dispersed in an aqueous continuous phase. Capsules of this nature and description have a variety of uses, such as for containing dyes, inks, chemical reagents, pharmaceuticals flavoring materials, fungicides, bactericides, pesticides, such as herbicides, insecticides, and the like, which substances can be dissolved, suspended or otherwise dispersed in or as the material to be enclosed by the polyurea capsule. The material to be encapsulated can be employed in the initial dispersion if a liquid, or heated to a temperature above its melting point if a solid, or dissolved or dispersed in suitable water-immiscible organic solvents. Once encapsulated, the liquid or other form is preserved until it is released by some means or instrumentality that breaks, crushes, melts, dissolves, or otherwise removes the capsular skin or until released by diffusion is effected under suitable conditions. Effective encapsulation by interfacial polymerization of an organic isocyanate intermediate can be accomplished in a process which utilizes two substantially immiscible liquids, one termed an aqueous phase and the other termed an organic phase, which comprises establishing a physical dispersion of the organic phase in the aqueous phase. Said organic phase contains the isocyanate intermediate for the polyurea capsule skin or enclosure. The interfacial polymerization, as it is termed, involves hydrolysis of an isocyanate monomer to form an amine, which in turn reacts with another isocyanate monomer to form the polyurea enclosure. During the hydrolysis of the isocyanate monomer, carbon dioxide is liberated. Capsules formed in this matter can range from 0.5 microns to about 100 microns.

SUMMARY OF THE INVENTION

It has been found that aqueous microcapsule flowable formulations of polyurea-encapsulated materials can be stablized by the addition of aluminum chloride hexahydrate or ferric chloride hexahydrate and adjustment of the pH of the solution to form the respective hydroxides which provide a stable dispersion in which the microcapsules will not separate and cake. The aluminum chloride hexahydrate or ferric chloride hexahydrate is easily added at the formulation stage without further additions and mixing prior to actual field use. For optimum physical stability, the aluminum hydroxide or ferric hydroxide should be used in conjunction with sequestering agents and a second suspending agent which will be further described hereinbelow. The class of materials encapsulated and the nature of the enclosure itself have little or no effect on the applicability of the suspension-buffer system preferred herein for the polyurea encapsulated flowable formulations. The system herein described will prevent any microcapsule system from separating and caking.

DETAILED DESCRIPTION OF THE INVENTION

When microcapsules with polyurea walls are formulated according to general practice of those skilled in the art, unstable suspensions may result. The microcapsules may tend to settle out and cake. Thereby, undesirable formulations result with characteristics which make their use in actual field conditions difficult. When the situation of settled and caked microcapsules is obtained, ordinary mixing and spraying equipment cannot satisfactorily be employed.

Therefore, it is a principle objective of this invention to produce a stable suspension system for microencapsulated materials. More specifically, this invention produces a stable suspension system for polyurea microencapsulated materials.

Another objective is to prevent settling and caking of microencapsulated material. More specifically, to prevent settling and caking of polyurea microencapsulated materials.

Other objectives will become apparent hereinafter.

It has now been found that polyurea microencapsulated materials are made into stable suspensions by a formulation comprising ferric hydroxide or aluminum hydroxide as a suspending and buffering agent, a second suspending agent and a sequestering agent. The formulation of the resulting polyurea microcapsules in this manner substantially eliminates settling and caking difficulties and produces a highly satisfactory flowable formulation.

In order to practice this invention, ferric chloride or aluminum chloride, as the hexahydrates or in solution, is added to aqueous suspension of polyurea microcapsules. The pH of the system is adjusted to from about pH 9.0 to about pH 12.0 with sodium hydroxide solution. This allows the formation of aluminum hydroxide or ferric hydroxide in situ. Effective stabilization and decreased caking by the formulation is obtained.

The formation of aluminum hydroxide or ferric hydroxide permits the system to act also as a buffer. In producing polyurea microcapsules from isocyanate intermediates, there is a small residual of isocyanate. This residual isocyanate when reacted with water causes the formation of carbon dioxide. If the pH value of the system shifts below about pH 8.0, then carbon dioxide pressure will develop in the system. The suspension-buffer systems presented in this invention form a high-capacity buffer which allows all of the carbon dioxide produced from the unreacted isocyanate to be converted to bicarbonate and carbonate ion without raising the pH of the system to an excessively high value. Therefore, by the presence of the buffer the pH is maintained within the preferred range of from about pH 9.0 to about pH 12.0.

Sequestering agents are materials which chelate or complex metallic ions in a reversible reaction to form a soluble complex molecule. the metal ion is effectively removed from the system. The resulting complex precludes the normal ionic effects and characteristics of the original metallic ion. Various agents can be used to sequester the metal ions in the present system, for example: polycarboxylic acids such as polyacrylic acid and the various hydrolyzed poly(methyl vinyl ether/maleic anhydride); aminopolycarboxylic acids, such as N-hydroxyethyliminodiacetic acid, nitrilotriacetic acid, N,N,N',N'-ethylenediaminetetraacetic acid, N-hydroxyethyl-N, N',N'-ethylenediaminetriacetic acid and N,N,N',N'',N'''-diethylenetriaminepentaacetic acid; α-hydroxy acids, such as citric acid, tartaric acid and gluconic acid; orthophosphates, such as trisodium phosphate, disodium phosphate, monosodium phosphate; condensed phosphates, such as sodium tripolyphosphate, tetrasodium pyrophosphate, sodium hexametaphosphate and sodium tetrapolyphosphate; 5-sulfo-8-hydroxyquinoline; and 3,5-disulfopyrocatechol. Primary function in this system is to sequester the metal ion, i.e. ferric or aluminum ions, thereby allowing gradual precipitation of the ferric hydroxide or aluminum hydroxide in the higher or basic pH range. The precipitate thus formed is in a suspended state. Preferred sequestering agents include sodium tripolyphosphate and hydrolyzed poly(methyl) vinyl ether/maleic anhydride) (Gantrez AN119).

For additional physical stability, the aluminum hydroxide or ferric hydroxide is used in conjunction with a second suspending agent, such as Attagel 40 ® or Biopolymer XB-23 ®. A suspending agent is a substance which aids in suspending the encapsulated material. These agents are satisfactory for suspending finely divided solids in water. In accomplishing satisfactory suspension of the encapsulated material, many various suspending agents can be employed, for example: colloidal minerals, such as silica ($SiO_2$), alumina ($Al_2O_3$), Montmorillonite clays, and attapulgite clay; polymeric-type suspending agents, such as natural gums, as guar gum, xanthan gum, gum arabic; alginates and carrageenan; and cellulose derivatives, as carboxymethyl cellulose and hydroxyethylcellulose; polyacrylic acid interpolymers; and high molecular weight hydrolyzed poly(methyl vinyl ether/maleic anhydride). Such suspending agents can suspend by thickening effects gelling effects and the like. The preferred suspending agents for use in the present invention are pseudoplastic (shear thinning) gelling agents and more preferably, Biopolymer XB-23 ® and Attagel 40 ®. Biopolymer XB-23 ® is a xanthan gum which is an anionic heteropolysaccharide produced by fermentation of a carbohydrate by the bacterium, *Xanthomonas compestris*. Attagel 40 ® is produced from attapulgite. It is a colloidal acicular mineral that can be described chemically as a hydrated magnesium aluminum silicate (3 $MgO$-1.5 $Al_2O_3$·$8SiO_2$·$9H_2O$).

The stable microcapsule suspension systems of this invention usually and preferably contain from about 0.1 to about 5.0 percent by weight of aluminum or ferric salt as aluminum trichloride hexahydrate or ferric chloride hexahydrate, from about 0.1 to about 5.0 percent by weight of a sequestering agent, and from about 0.01 to about 5.0 percent by weight of a second suspending agent. Where required, varying amounts (percentages by weight) of inert material can be used to improve the characteristics of the resulting suspensions.

The following specific examples illustrate the invention which are not limiting in nature. All compositions are described in parts by weight. The microcapsules were prepared according to the process described in Belgian Pat. No. 796,746 published Sept. 14, 1973.

EXAMPLE I

Microcapsules containing 48.0 parts Sutan ® (S-ethyl diisobutylthiocarbamate) and 3.9 parts polyurea wall were produced in 41.75 parts water, 1.0 part Gantrez AN119, 0.2 parts Tergitol 15-S-7 (a linear alcohol ethoxylate emulsifier), and 0.1 parts defoamer. Sodium tripolyphosphate (2.0 parts), Attagel 40 ® (0.5 parts) and Dowcide G (0.05 parts) (sodium pentachlorophenate) were then added to the microcapsule dispersion and dispersed well with a mechanical disperser. The pH of the dispersion was adjusted to 9.5 with 50 percent sodium hydroxide. $AlCl_3$·$6H_2O$ (0.5 parts) was added next to the dispersion and dispersed well with the mechanical disperser.

One gallon of the above-described formulation was stored under ambient conditions for two months. At the end of the two month period the container was inverted twice. The formulation was homogeneous and was easily poured from the container. There was no observable caking or lumping. The formulation dispersed readily even in ice water (0° C.).

EXAMPLE II

Microcapsules containing 36.0 parts Vernam ® (S-propyl-dipropylthiocarbamate), 3.0 parts N,N-diallyldichloroacetamide (an herbicide antidote) and 3.2 parts polyurea wall were produced in 53.95 parts water, 1.0 part Gantrez AN119, 0.2 parts Tergitol 15-S-7 and 0.1 parts defoamer. Sodium tripolyphosphate (0.8 parts), Attagel 40 ® (1.0 part) and Dowcide G (0.05 parts) then were added to the microcapsule dispersion and dispersed well with a mechanical disperser. $FeCl_3$·$6H_2O$ (0.7 parts) was next added to the dispersion as a 64 percent aqueous solution and dispersed well with a mechanical disperser. The pH of the dispersion then was raised to 11.0 with 50 percent sodium hydroxide.

One gallon of the above-described formulation was stored under ambient conditions for three and one-half months. At the end of the three and one-half month period, the container was inverted twice. There was no observable caking in the container and the contents could be mixed easily. The walls of the empty container were clean.

EXAMPLE III

Microcapsules containing 48.0 parts Sutan ® (S-ethyl diisobutylthiocarbamate), 2.0 parts N,N-diallyldichloroacetamide (herbicide antidote) and 4.05 parts polyurea wall were produced in 44.12 parts water, 1.0 part Gantrez AN119 and 0.2 parts Tergitol 15-S-7. Sodium tripolyphosphate (0.03 parts), Xanthan Gum Biopolymer XB-23 (0.05 parts) and Dowcide G (0.05 parts) were then added to the microcapsule dispersion and dispersed well with a mechanical disperser. $FeCl_3 \cdot 6H_2O$ (0.5 parts next was added to the dispersion as a 64 percent aqueous solution maintaining the pH between 4.5 and 5.0 with sodium hydroxide and the resulting $Fe(OH)_3$ dispersed with a mechanical disperser. The pH was raised to 11.0 with 50 percent sodium hydroxide and the resulting $Fe(OH)_3$ was dispersed well with the mechanical disperser.

One gallon of the above-described formulation was stored under ambient conditions for three months. At the end of the three month period the bottle was inverted twice and the contents poured out. There was no observable evidence of caking and no residual ring on the container wall. The formulation dispersed readily in cold water. When sprayed through nozzles backed with 50 mesh screens, there was no clogging of the nozzles and the screens were clean.

EXAMPLE IV

Microcapsules containing 44.7 parts Dyfonate ® (O-ethyl-S-phenyl ethylphosphonodithioate) and 7.9 parts polyurea wall were produced in 42.55 parts water, 1.0 parts Gantrez AN119, 0.2 parts Tergitol 15-S-7 and 0.1 parts of defoamer. Sodium tripolyphosphate (2.0 parts), Attagel 40 ® (0.5 parts) and Dowcide G (0.05 parts) were then added to the microcapsule dispersion and dispersed well with a mechanical disperser. $AlCl_3 \cdot 6H_2O$ (1.0 parts) next was added to the dispersion as a 50 percent aqueous solution and dispersed well with a mechanical disperser. The pH of the dispersion then was raised to 11.0 with 50 percent sodium hydroxide.

One gallon of the above-described formulation was stored under ambient conditions for three months. At the end of the three month period, the container was inverted. There was no observable caking on the bottom of the container. The contents of the container could be mixed easily.

The stable suspension system for microencapsulated flowable formulation has been described by reference to certain illustrative examples employing specific encapsulated ingredients. Various modifications have been set forth herein and other modifications will be apparent to those skilled in the art. Any such modifications are intended to be within the spirit and scope of the invention as defined by the appended claims.

What is claimed is:

1. A stable aqueous suspension of microencapsulated material comprising microcapsules, a suspending and buffering agent selected from the group consisting of ferric hydroxide and aluminum hydroxide, a sequestering agent, a second suspending agent, the pH of said suspension adjusted to from about pH 9.0 to about pH 12.0.

2. A stable aqueous suspension of microencapsulated material comprising microcapsules with polyurea walls, a suspending and buffering agent selected from the group consisting of ferric hydroxide and aluminum hydroxide, a sequestering agent, a second suspending agent and the pH of said suspension adjusted to from about pH 9.0 to about pH 12.0.

3. A stable suspension according to claim 2 in which said sequestering agent is selected from the group consisting of polycarboxylic acids, aminopolycarboxylic acids, α-hydroxy acids, orthophosphates, condensed phosphates, 5-sulfo-8-hydroxyquinoline and 3,5-disulfopyrocatechol and said second suspending agent is selected from the group consisting of colloidal minerals and polymeric-type suspending agents.

4. A stable suspension according to claim 3 in which said second suspending agent is selected from the group consisting of silica, alumina, Montmorillonite clays, attapulgite clay, guar gum, xanthan gum, gum arabic, alginates, carrageenan, carboxymethyl cellulose and hydroxyethyl cellulose.

5. A stable suspension according to claim 2 in which said sequestering agent is selected from the group consisting of sodium tripolyphosphate and hydrolyzed poly(methyl vinyl ether/maleic anhydride) and a second suspending agent is selected from the group consisting of a xanthan gum and colloidal attapulgite: hydrated magnesium aluminum silicate.

6. A stable suspension according to claim 5 wherein said suspending and buffering agent is from about 0.1 to about 5.0 percent by weight of aluminum or ferric salt as aluminum trichloride hexahydrate or ferric chloride hexahydrate, the sequestering agent is from about 0.1 to about 5.0 percent by weight and the second suspending agent is from about 0.01 to about 5.0 percent by weight.

7. A stable suspension according to claim 2 wherein the microencapsulated material is a herbicide.

8. A stable suspension according to claim 2 wherein the microencapsulated material is an insecticide.

9. The method of preparing a stable suspension of microcapsules comprising the addition to a microcapsule dispersion a sequestering agent and a suspending and buffering agent selected from the group consisting of aluminum chloride and ferric chloride, and a second suspending agent and adjusting the pH of said suspension to from about pH 9.0 to about pH 12.0 to form aluminum hydroxide and ferric hydroxide in situ.

10. The method according to claim 9 in which said sequestering agent is selected from the group consisting of polycarboxylic acids, aminopolycarboxylic acids, α-hydroxy acids, orthophosphates, condensed phosphates, 5-sulfo-8-hydroxyquinoline and 3,5-disulfopyrocatechol and said second suspending agent is selected from the group consisting of colloidal minerals and polymeric-type suspending agents.

11. The method according to claim 9 in which said second suspending agent is selected from the group consisting of silica, alumina, Montmorillonite clays, attapulgite clay, guar gum, xanthan gum, gum arabic, alginates, carrageenan, carboxymethyl cellulose and hydroxyethylcellulose.

12. The method according to claim 9 in which sodium hydroxide is used to adjust the pH of the system.

13. The method according to claim 9 in which said sequestering agent is selected from the group consisting of sodium tripolyphosphate and hydrolyzed poly(methyl vinyl ether/maleic anhydride) and said second suspending agent is selected from the group consisting of a xanthan gum and colloidal attapulgite; a hydrated magnesium aluminum silicate.

14. The method of claim 9 in which said microcapsules contain a herbicide.

15. The method of claim 9 in which said microcapsules contain an insecticide.

16. The method of claim 9 in which said microcapsules contain a herbicide and antidote therefor.

* * * * *